US006358275B1

(12) United States Patent
McIlroy et al.

(10) Patent No.: US 6,358,275 B1
(45) Date of Patent: Mar. 19, 2002

(54) TISSUE-DERIVED VASCULAR GRAFTS AND METHODS FOR MAKING THE SAME

(75) Inventors: Brian K. McIlroy, Georgetown, TX (US); Tim Ashton, West Kilbride; Roshan Maini, Bridge of Weir, both of (GB); Richard E. Phillips, San Marcos, TX (US)

(73) Assignee: Sulzer Carbomedics Inc., Austin, TX (US)

(*) Notice: Subject to any disclaimer, the term of this patent is extended or adjusted under 35 U.S.C. 154(b) by 0 days.

(21) Appl. No.: 09/411,494

(22) Filed: Oct. 4, 1999

(51) Int. Cl.⁷ .................................................. A61F 2/06
(52) U.S. Cl. ................ 623/1.28; 623/1.49; 623/23.58; 623/23.72; 600/36
(58) Field of Search ............................. 623/1.28, 1.49, 623/23.72, 23.58; 600/36

(56) References Cited

U.S. PATENT DOCUMENTS

| 3,878,565 A | | 4/1975 | Sauvage .............................. 3/1 |
| 3,945,052 A | | 3/1976 | Liebig ................................. 3/1 |
| 4,047,252 A | | 9/1977 | Liebig et al. ..................... 3/1.4 |
| 4,415,523 A | * | 11/1983 | Barham et al. .......... 264/342 R |
| 4,517,687 A | | 5/1985 | Liebig et al. ..................... 3/1.4 |
| 4,892,539 A | | 1/1990 | Koch .............................. 623/1 |
| 5,776,182 A | * | 7/1998 | Bruchman et al. ............ 623/1.1 |
| 5,854,397 A | | 12/1998 | Mechanic ..................... 530/356 |
| 6,187,038 B1 | * | 2/2001 | Sullivan et al. ............. 623/1.43 |

OTHER PUBLICATIONS

Moore, M. M., et al., "Stabilization Pericardial Tissue by Dye-Mediated Photooxidation", Journal of Biomedical Materials Research, vol. 28, 611–618 (1994).
Oster, G., et al., "Dye Sensitized Photooxidation",J. Am. Chem. Soc., Oct. 5, 1959, vol. 81, pp. 5095–5099.
Khor, E., "Methods for the Treatment of Collagenous Tissues for Bioprostheses", Biomaterials 18 (1997) 95–105.

* cited by examiner

Primary Examiner—Corrine McDermott
Assistant Examiner—Choon P. Koh
(74) Attorney, Agent, or Firm—Timothy L. Scott

(57) ABSTRACT

Vascular grafts, and methods for making the same, are provided. The vascular grafts comprise a graft tissue derived from a biological source that is enclosed within an external synthetic sleeve. The synthetic sleeve has an extended length that is greater than the length of the graft tissue. However, the sleeve is longitudinally compressed such that it has a resting length substantially similar to the length of the graft tissue.

59 Claims, 1 Drawing Sheet

TISSUE-DERIVED VASCULAR GRAFTS AND METHODS FOR MAKING THE SAME

BACKGROUND OF THE INVENTION

1. Field of the Invention

This invention relates generally to prosthetic devices for use in the reconstruction and/or repair of the human vascular system. More particularly, the invention relates to vascular grafts derived from biological tissues, and methods of making the same.

2. Description of the Related Art

Vascular grafts have become widely used for replacing diseased arteries in humans. For example, a blocked portion of an artery can be surgically excised and a tubular shaped vascular graft implanted in its place. Alternatively, a vascular graft may be used to bypass a diseased vessel entirely. Among the most common vascular graft prostheses are those formed from synthetic biologically compatible materials in a tubular form which retain an open lumen to permit blood to flow through the graft after implantation. The biologically compatible materials typically used to produce synthetic vascular grafts have included thermoplastic materials such as polyesters, polytetrafluoroethylene (PTFE), silicon and polyurethanes.

Unfortunately, certain limitations have been associated with the use of synthetic vascular grafts. For example, synthetic grafts are often highly susceptible to neointimal hyperplasia and late graft thrombosis. Moreover, many synthetic grafts have a relatively high porosity and must be pre-clotted prior to implantation to avoid extensive hemorrhage. This pre-clotting procedure is not always practical or successful.

In addition, many synthetic vascular grafts have a tendency to kink or collapse when the graft is twisted or bent during or subsequent to implantation. To address this problem, many synthetic grafts are subjected to a crimping process. Crimping involves forming ridges in the walls of the grafts to minimize the likelihood of kinking or collapse of the tubing when flexed. Most crimping processes result in uniform, regular, circular corrugations along the length of the graft which help maintain a more uniform strength over the surface of the graft tubing. For example, U.S. Pat. No. 3,878,565 describes a tubular textile synthetic fiber prostheses wherein the graft body is crimped into regular, circumferential corrugations. U.S. Pat. Nos. 3,945,052, 4,047,252, and 4,517,687 describe knit and woven grafts that are circularly crimped. U.S. Pat. No. 4,892,539 describes a graft that is crimped in a spiral fashion.

To overcome some of the limitations associated with synthetic vascular grafts, grafts derive from biological tissues have also been under investigation. These grafts are typically derived from animal tissues which have been treated by a suitable process such as a chemical or photo-fixation procedure in order to stabilize the tissue and to improve its biocompatibility. However, tissue-derived arteries can be susceptible to degradation in vivo resulting in aneurysm and device failure. To provide protection in the event of aneurysm, the tissue graft may be enclosed within a tubular external sleeve. This sleeve may be slightly oversized with respect to the outer diameter of the graft and made from a non-compliant, expanding material that is resistant to degradation upon implantation. In the event of a growing aneurysm, the sleeve serves to contain the artery and prevent bursting of the graft.

However, we have found that the use of tissue-derived grafts in combination with synthetic external sleeves, presents a unique obstacle. Although it is desired to provide a tissue artery which retains the longitudinal compliance of a natural tissue, upon inserting the compliant tissue graft within a substantially non-compliant synthetic sleeve, there is a mismatch of the sleeve to tissue length once the graft is pressurized. Moreover, our attempts to match the compliance of the sleeve with that of the tissue graft using conventional crimping procedures resulted in vascular grafts having incomplete healing responses following implantation.

The present invention is directed to providing tissue-derived vascular grafts which overcome, or at least reduce the effects of, one or more of the problems set forth above.

SUMMARY OF THE INVENTION

In one aspect of the present invention, a vascular graft is provided which comprises a length of vascular tissue having a tubular structure and a synthetic sleeve enclosing the vascular tissue. The synthetic sleeve has an extended length and a relaxed length, in which the relaxed length is less than the extended length and the relaxed length is substantially similar to the length of vascular tissue. The relaxed length of the synthetic sleeve is typically between about 50% and 95% of the extended length of the synthetic sleeve, more typically between about 70% and 90% of the extended length of the synthetic sleeve, and preferably between about 75% and 85% of the extended length of the synthetic sleeve.

It has been found that it can be beneficial to provide crimps along at least some portion of the longitudinal length of the synthetic sleeve. The crimps are preferably circumferential crimps that are substantially rounded, i.e., do not have any angular features which give rise to void spaces between the sleeve and the graft tissue following implantation and pressurization of the device.

The graft tissue of the vascular graft may be derived from any of a variety of biological sources, e.g. human, bovine, porcine, ovine, equine, canine or goat. Vascular tissue derived from a carotid artery or thoracic artery, for example from a bovine, are particularly suitable. Prior to use in a vascular graft of this invention, the tissue is treated by one or more fixation techniques to stabilize the tissue. The fixation of the tissue may be performed by any of a variety of conventional approaches, such as chemical fixation using glutaraldehyde, or, preferably, by a photooxidation or other process which allows for some retention of the mechanical compliance of the native tissue before fixation.

The synthetic sleeve may be comprised of a wide range of polymeric materials that can be woven, knitted or braided polymeric fibers or yarns in the form of a tubular structure. These may include polyesters, polypropylenes, polyethylenes, polyurethanes, and other like materials. Preferably, the synthetic sleeve is comprised of polyethylene terepthalate or polytetrafluorethylene.

In a further aspect of the invention, there is provided a method for making a vascular graft, in which a tubular polymeric sleeve, e.g., a polyethylene terepthalate or polytetrafluoroethylene sleeve, is longitudinally compressed to a length less than about 50% of its initial length and exposed to a first heat treatment to introduce crimps in the sleeve. Thereafter, the sleeve is stretched longitudinally to a length between about 70% and 90% of its initial length and exposed to a second heat treatment to lessen the crimps and thereby provide substantially rounded crimps. A length of vascular tissue, preferably photooxidized vascular tissue, is thereafter inserted within the sleeve to provide a vascular graft device.

BRIEF DESCRIPTION OF THE DRAWINGS

The invention may be best understood by reference to the following description taken in conjunction with the accompanying drawings, in which like reference numerals identify like elements, and in which.

Figure 1:
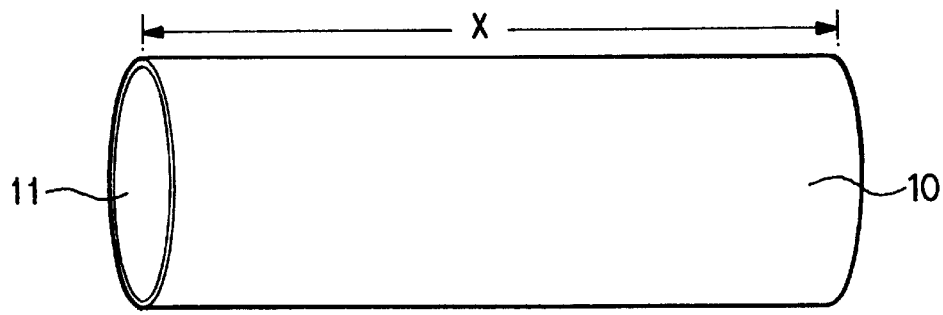
FIG. 1 is a simplified representation of a length of tubular vascular tissue.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF ILLUSTRATIVE EMBODIMENTS

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 2:
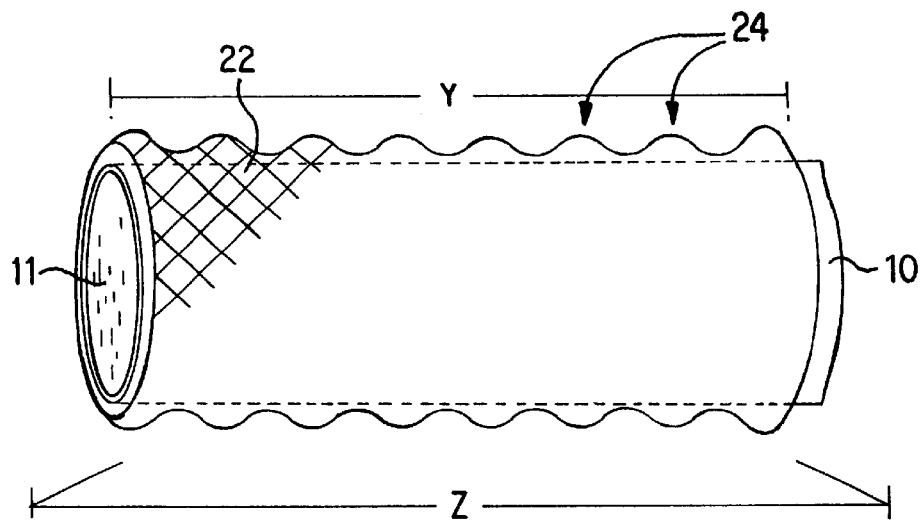
FIG. 2 shows the vascular tissue inserted within a tubular synthetic sleeve having substantially rounded crimps.

FIG. 1 represents a simplified illustration of a section of graft tissue 10 defining a lumen 11 and having a length X to be used in constructing a vascular graft according to this invention. In FIG. 2, the graft tissue 10 is shown inserted into and thereby substantially enclosed within an illustrative external synthetic sleeve 22 having a relaxed length Y and an extended length Z. The relaxed length Y is the length of the sleeve produced according to the invention in its resting state where no longitudinal forces are present. The extended length Z of the synthetic sleeve 22 represents it length upon stretching the sleeve 22 longitudinally. The synthetic sleeve 22 at its relaxed length Y has a plurality of rounded crimps 24 comprising wave-like undulations apparent when viewing the device from its side. According to the present invention, we have found that when constructing tissue-derived vascular grafts having external synthetic sleeves, the relationship between the length X of the graft tissue sample 10, the relaxed length Y of the synthetic sleeve 22 and the extended length Z of the synthetic sleeve 22 are important in providing a vascular graft device having the desired properties. The invention thereby provides a vascular graft wherein the graft tissue is longitudinally compliance-matched with the synthetic sleeve. Moreover, we have found that the nature of the surface configuration of the synthetic sleeve following insertion of the graft tissue into the sleeve is an important determinant of vascular graft compatibility with the host following implantation.

Therefore, according to the present invention, the extended length Z of the synthetic sleeve 22 is greater than its relaxed length Y. In addition, the relaxed length Y of the synthetic sleeve 22 is substantially similar, e.g., within about ±10%, preferably slightly shorter than, the graft tissue length X. How much greater the extended sleeve length Z is than the relaxed sleeve length Y will vary depending on a number of factors, such as the mechanical properties of the tissue being used, e.g., its longitudinal compliance, the method by which the tissue is treated, e.g., by fixation, and the properties of the material from which the external sleeve is fabricated. Most typically, however, the relaxed length Y of the synthetic sleeve 12 will be about 50% to 95% of its extended length Z, preferably about 70% to 90% of its extended length Z, more preferably about 75% to 85% of its extended length Z.

In order to provide a synthetic sleeve with a resting length Y, a tubular synthetic sleeve sample having a length similar to Z (e.g., ±10%) is treated in a manner to provide a degree of longitudinal compaction along some or all of its length. One way this may be achieved is by employing certain crimping techniques that have been used for fabricating vascular grafts produced from synthetic materials. For example, in one illustrative method, a synthetic sleeve, such as a woven Dacron sleeve, is placed on a bar/mandrel. A bar having a diameter slightly smaller (e.g., by about 0.1–1.0 mm) than the diameter of the synthetic sleeve may be desired where the sleeve is subject to shrinkage to take into account the shrinkage during washing. Crimps are produced in the sleeve by longitudinally compacting the sleeve on the bar to a certain extent, for example using a mechanical rig. If desired, thread can be wound around the sleeve prior to compaction at a selected tension and/or pitch along its length to facilitate the location and configuration of the crimps. Once the sleeve has been longitudinally compressed on the bar to a desired extent, the ends are secured, e.g., using spring clips, and the sleeve is heated to cause the formation of circular, circumferential crimps along the length of the sleeve. An autoclave cycle of about 15 minutes reaching a maximum temperature of about 140° C. has been found suitable for introducing the crimps, however the skilled individual in the art will appreciate that many variations of temperature, time and pressure may be used to achieve a similar result. For example, the sleeve in one illustrative embodiment is heated at a temperature in the range of about 110 to 140 degree C. at a pressure from about 10 to 25 psi for a time sufficient to introduce the desired crimps, typically between about 0.1 and 0.5 hours. Moreover, although the process described above introduces circumferential crimps in the sleeve, there are various means by which they can be introduced in different configurations and geometries, e.g., spiral crimps, and these may also be suitable for use in this invention.

Figure 3:
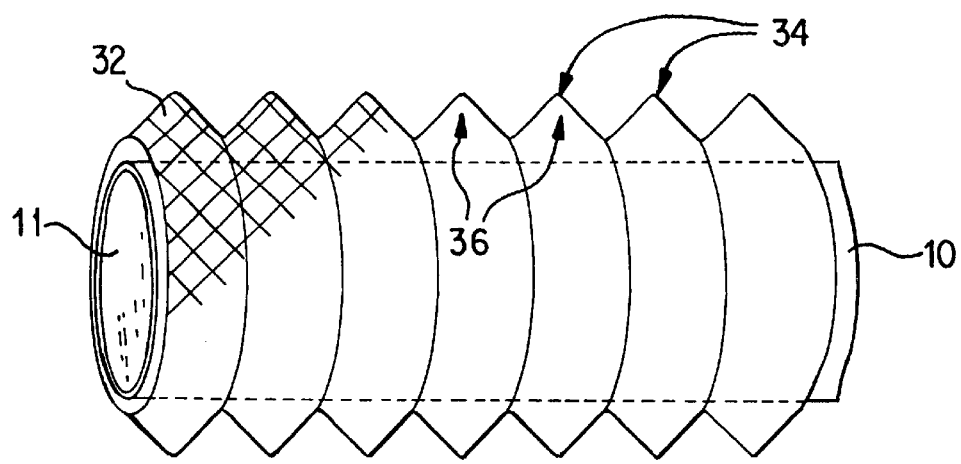
FIG. 3 shows the vascular tissue inserted within a tubular synthetic sleeve having substantially angled crimps.

Many crimping procedures, such as the one described above, give rise to sharp edges/angles in the synthetic sleeve similar to the angular crimps 34 on synthetic sleeve 32 shown in FIG. 3. However, we have found that for tissue-derived vascular grafts having external synthetic sleeves, it is preferred that the longitudinal compaction of the sleeve does not result in crimps having these angles or other similar geometries. Upon surgical implantation and pressurization of the vascular graft device, the graft tissue expands longitudinally to an extent dependent on the type of tissue used and the fixation method employed. Upon longitudinal expansion of the graft tissue, the synthetic sleeve also stretches as a result of its crimping pattern. Thus, by providing an appropriate crimping pattern in the sleeve which allows it to expand longitudinally to a similar extent as the longitudinal expansion of the graft tissue, the tissue and the sleeve are substantially compliance matched.

However, if the sleeve has crimps such as the angular crimps 34 shown in FIG. 3, the angled spaces 36 can give rise to void spaces between the synthetic sleeve 32 and the graft tissue 10 following implantation and pressurization of the device. These void spaces resulting from the angular crimps, or any other sleeve geometries which give rise to void spaces between the sleeve and the tissue following implantation and pressurization, can lead to poor device compatibility with the host. In particular, granulation tissue can form in the void spaces, and, in the presence of macrophages, may extend into the wall of the graft tissue leading to periadventitial degradation of the tissue. Thus, according to the present invention, it is preferred that the process by which the sleeve is longitudinally compacted to arrive at the relaxed length Y is one that results in a sleeve surface configuration having substantially rounded crimps, i.e., those which minimize the presence of void spaces between the sleeve and tissue following implantation and pressurization of the device.

The desired synthetic sleeve having a relaxed length Y and having the desired rounded crimps may be achieved by any suitable approach. For example, one may employ a crimping procedure which directly provides the desired surface configuration and length Y, or, alternatively, one could employ a two-step process comprising a conventional crimping process followed by a treatment subsequent to the crimping process to lessen any undesirable angles that may be present. For example, in one illustrative embodiment, a sleeve is subjected to a crimping process, such as that described above, wherein the sleeve is longitudinally compacted on the bar to a length less than relaxed length Y, heat treated to introduce angular crimps. Thereafter, the sleeve is subjected to a further treatment wherein the sleeve is stretched on the bar to a length similar to Y (e.g., ±10% of Y) and subjected to a further heat treatment to remove or minimize the angular crimps. This second heat treatment, as with the first, may utilize a variety of combinations of time, temperature and pressure to achieve its objective. This approach provides a sleeve having the desired relaxed length Y and having substantially rounded crimps along the surface of the sleeve, such as the rounded crimps 24 shown in FIG. 2. Subsequent to the crimping processes, the sleeve may be treated, as desired, e.g., by a fluoropassivation process, to impart other desirable properties and/or characteristics.

SYNTHETIC SLEEVE

The synthetic sleeve which encloses the graft tissue according to this invention may be comprised of many types of polymeric materials and may be made by any of a number of conventional approaches known in the art. The sleeve is generally fabricated by techniques of weaving, knitting and/or braiding polymeric fibers or yarns in the form of a desired tubular or substantially tubular structure which defines an interior lumen. The fibers may be, for example, flat, twisted or textured, and may be of the multifilament, monofilament or spun type. Although there is wide latitude in the selection of the polymeric materials used to make the sleeve, e.g., polyesters, polypropylenes, polyethylenes, polyurethanes, and the like, particularly preferred materials include polyethylene terepthalate (Dacron), polytetrafluoroethylene (Teflon).

The internal diameter of the tubular synthetic sleeve will of course vary depending on the intended application. Typically, the internal diameter of the sleeve will be in the range of about 1 mm to about 25 mm, most typically between about 5 mm and 15 mm. The internal diameter of the sleeve is usually selected to be slightly larger than the outer diameter of the graft tissue being used. For example, using photooxidized tissue grafts (which retain some degree of radial compliance), we have found it suitable to use a sleeve having an 8 mm diameter for tissue grafts having diameters of about 4 mm to 7 mm, an 10 mm sleeve for arteries having diameters between about 7 mm and 9 mm, etc.

The length of the sleeve will depend on the length of the graft tissue being used, but will typically be in the range of ±10% of the length of the graft tissue. It may be preferred for some applications to use a sleeve that is shorter than the graft tissue so that the sleeve can be pulled over the graft tissue and sutured separately.

GRAFT TISSUE

The graft tissue component of the vascular graft devices of the invention may be derived from essentially any biological tissue of interest provided the tissue has the proper geometrical dimensions and/or configurations for its intended application. Typically, the graft tissue will be comprised of vascular tissue removed from a human or from an animal species, e.g., bovine, porcine, ovine, equine, canine, goat, etc., and may be removed from various anatomical positions within the body. For example, the graft tissue may be derived from carotid arteries, thoracic arteries, mammary arteries, to name a few. In one preferred embodiment of the invention, the tissue graft is derived from a bovine carotid artery. The graft tissue will have a structure, e.g., a tubular structure, which defines an interior lumen having dimensions sufficient for allowing blood to flow therethrough following implantation.

The primary component of the biological tissues used to fabricate bioprostheses is collagen, a generic term for a family of related extracellular proteins. Collagen molecules consists of three chains of poly (amino acids) arranged in a trihelical configuration ending in non-helical carboxyl and amino termini. These collagen molecules assemble to form microfibrils, which in turn assemble into fibrils, resulting in collagen fibers. The amino acids which make up the collagen molecules contain side groups, including amine ($NH_2$), acid (COOH) and hydroxyl (OH) groups, in addition to the amide bonds of the polymer backbone, all of which are sites for potential chemical reaction on these molecules.

Because collagenous tissues degrade very rapidly upon implantation, it is necessary to stabilize the tissue if it is to be implanted into a living system. The tissue can be stabilized by any of a variety of conventional approaches. For example, chemical stabilization by tissue cross-linking, also referred to as tissue fixation, can be achieved using bi-functional and multi-functional molecules having reactive groups capable of forming irreversible and stable intramolecular and intermolecular chemical bonds with the reactive amino acid side groups present on the collagen molecules. An additional method for the fixation/stabilization of the graft tissues involves a photooxidation process.

PHOTOOXIDATION OF GRAFT TISSUE

In one preferred embodiment of the invention, the biological tissue used to provide the graft tissue component of the vascular graft of the invention is treated by a photooxidation process. The photooxidation may be carried out according to conventional methodologies. Suitable photooxidation process have been described, for example in U.S. Pat. No. 5,854,397, the disclosure of which is incorporated herein by reference, and in Moore et al. (1994). The photooxidation process provides an efficient and effective method for cross-linking and stabilizing various proteinaceous materials including, but not limited to, collagen, collagen fibrils and collagen matrices. The term proteinaceous material as used herein includes both proteins such as collagen and protein-containing materials such as tissues. The material to be cross-linked is generally provided as a vascular tissue sample. Such materials are harvested from the donor animal and immediately immersed in cold buffered saline for storage, with frequent rinses and/or changes with fresh saline, until a fixation process is performed.

The vascular tissue material to be photooxidized is then immersed, dispersed, or suspended (depending upon its previous processing) in an aqueous media for processing. Suitable media for immersion of the material (for purposes of convenience, the word "immersion" shall be considered to include suspension and/or solubilization of the proteinaceous material) include aqueous and organic buffer solutions having a neutral to alkaline pH, preferably a pH of about 6.5 and above because of the denaturation caused by acid pH. Particularly preferred are buffered aqueous solutions having a pH of from about 6.8 to about 8.6.

In a particularly preferred photooxidation process, two media solutions are utilized for what is referred to herein as "preconditioning" the vascular tissue material before irradiation. The material is "preconditioned" in the sense that tissue soaked in the first media solution and irradiated in the second are apparently better cross-linked, e.g., they show improved mechanical properties and decreased susceptibility to proteolytic degradation. The efficacy of this preconditioning is affected by the osmolality of the first media solution, it being preferred that solutions of high osmolality be used as the first media solution. Particularly preferred are sodium potassium, or organic buffer solutions such as sodium, chloride, sodium phosphate, potassium chloride, potassium phosphate, and Good's buffers having a pH of from about 6.8 to about 8.6, the osmolality of which have been increased by addition of a solute such as 4M sucrose or other soluble, high molecular weight carbohydrate to between about 393 mosm and about 800 mosm.

The solute added to increase the osmolality of the first media may have an adverse effect on the degree of cross-linking of the product when present during irradiation. Consequently, after soaking in the first media, the tissue is preferably removed therefrom and immersed in a second media for irradiation. The second media is preferably an aqueous buffered solution having a pH of from about 6.8 to about 8.6 in which the photo-catalyst is dissolved. Preferred second media are sodium and potassium phosphate buffers having a pH of from about 7.4 to about 8.0 and an osmolality of from about 150 to about 400 mosm, 300 ±10 mosm being particularly preferred.

The tissue may be advantageously immersed sequentially in the first media and then in the catalyst-incorporated second media prior to photooxidation for a total period of time sufficient to allow tissue, dye, and medium to reach equilibrium. When the ratio of the concentration of the medium to that of the material to be cross-linked is in the range of from about 10:1 to 30:1, equilibrium can generally be readily achieved. The ratio of the concentrations is generally not critical, and may be adjusted up or down as desired. Once an equilibrium is reached, the sample is photooxidized in the catalyst-incorporated medium. The time required to reach equilibrium varies depending upon such factors as, for instance, the temperature of the media solutions, the osmolality of the first media, and the thickness of the tissue or other sample of proteinaceous material. A period of time as short as a few minutes or as long as several days may be sufficient, but it has been found that periods of from minutes to hours duration is generally sufficient to allow sufficient time for most collagenous materials and media to equilibrate.

The catalysts for use in the photofixation process include photooxidative catalysts (photo-catalysts) that when activated will cause transfer of electrons or hydrogen atoms and thereby oxidize a substrate in the presence of oxygen. Although varied results are possible depending upon the particular catalyst utilized, appropriate catalysts include, but are not limited to, those listed in Oster, et al., J. Am. Chem. Soc. 81: 5095, 5096 (1959). Particularly preferred catalysts include methylene blue, methylene green, rose bengal, riboflavin, proflavin, fluorescein, eosin, and pyridoxal-5-phosphate.

The concentration of catalyst in the media will vary based on several process parameters, but should be sufficient to insure adequate penetration into the material to be cross-linked and to catalyze the photooxidation of the protein. A typical catalyst concentration ranges from about 0.0001%–0.25% (wt/vol); the preferred concentration ranges from about 0.001 to about 0.01%.

To achieve maximum cross-linking and stabilization of the vascular tissue, the following steps may be taken: (1) the photooxidative catalyst should be completely solubilized in the reaction medium prior to use to ensure that the desired dye concentration is achieved; (2) the concentration of the catalyst in the tissue or suspension should be in equilibrium with that in the surrounding medium; and (3) the catalyst solution should be filtered to remove any sizable particulate matter, including chemical particulates, therefrom.

Because the photofixation process involves primarily an oxidative reaction, to assure completion of the reaction, an adequate supply of oxygen must be provided during photooxidation. While an oxygen concentration of about 20% by volume (referring to the concentration of oxygen in the atmosphere over the media) is preferred to assure sufficient dissolved oxygen in the media to prevent oxygen content from becoming rate limiting, all concentrations >0% can also be used. Depending upon the temperature at which the material is held during exposure to light, the oxygen requirement can be met, for instance, by agitating the solution or otherwise mixing the solution, suspension, or sample during the reaction process. Oxygen concentration in the atmosphere over the media during irradiation is preferably maintained in the range of from about 5% to about 40%. Such concentrations (again depending upon temperature) can also be achieved, for instance, by bubbling air into the media during irradiation of the tissue or, if concentrations higher than about 20% are desired, by bubbling oxygen mixtures or air having an increased oxygen content into the media.

As with other catalytic or kinetic-type reactions, the temperature at which the reaction is run directly affects the reaction rate and the oxygen available in the media. Tests conducted with various media ranging in pH from about 6.8 up to about 7.4 and having an osmolality of 300 ±10 mosm indicate that as the temperature of the media increases from about 4 degree C. to about 50 degree C., oxygen concentration drops in roughly linear fashion from about 11–12 ppm to about 5 ppm. The dye-catalyzed photooxidation process is exothermic, and it is, therefore, preferred that a relatively constant temperature be maintained during irradiation of the proteinaceous material to prevent denaturation of the proteinaceous material and the driving of the oxygen out of the media by the increase in temperature. Usually, a recirculating bath is sufficient to maintain and control the temperature within the jacketed reaction vessel or chamber but placement of the reaction chamber within a controlled environment such as a refrigerator or freezer will work as well. As disclosed herein, photooxidation conducted at temperatures ranging from about 2 degree C. to +40degree C. has been shown to be effective; the preferred temperatures are from about 0 degree to about 25 degree C. To prevent or alleviate denaturation of the protein comprising the vascular tissue, temperatures below the denaturation temperature of that protein are preferred. Likewise, temperatures above the freezing point of the reaction medium are also preferred.

The process is conducted at temperatures low enough to avoid heat denaturation and pH high enough to avoid acid denaturation of the collagen or other proteinaceous material during cross-linking. Likewise, temperature is held at a level sufficient to maintain the oxygen concentration in the media in which the proteinaceous material is immersed during irradiation.

Once the tissue is prepared, it is photo-irradiated, preferably in a controlled system wherein temperature, distance to light source, irradiation energy and wavelength, oxygen concentration and period of irradiation can be monitored and/or maintained. The tissue is photo-irradiated under conditions sufficient to cause cross-linking. Photooxidation is generally achieved using incandescent, white light or fluorescent light, i.e., visible light, or that portion of light in the visible range that is absorbed by the catalyst.

The intensity of the light employed, and the length of time required to cross-link a given proteinaceous material will vary depending upon several factors. These include: (1) the type and amount of proteinaceous material; (2) the thickness of the tissue sample; (3) the distance between the proteinaceous material and the irradiation source; (4) the catalyst employed; (5) the concentration of catalyst; and (6) the type and intensity of the light source. For instance, exposure time may vary from as little as a few seconds up to as much as about 160 hours. With regard to the intensity of the light, one or more lights may be used of intensity preferably ranging up to about 150 watts, preferably held at a distance from about 2.5 cm to 12 cm from the sample surface. Greater exposure time is required when fluorescent or lower power lights are utilized. These ranges are quite variable; however, they may be easily determined for a given material without resort to undue experimentation.

Evidence of the cross-linking of the vascular tissue by photooxidation may be provided by several approaches. For instance, polyacrylamide gel electrophoresis of the irradiated material in sodium dodecylsulfate (for example, 0.1%) evidences such cross-linking by a significant decrease in the amount of lower molecular weight material with the simultaneous appearance of high molecular weight material.

Further evidence of cross-linking may be provided by known solubility and digestibility tests. For instance, cross-linked collagen is generally insoluble such that solubility tests provide direct evidence of the degree of cross-linking. The digestibility tests involve incubation of the proteinaceous product with a proteolytic enzyme such as papain, trypsin, pepsin, or bacterial collagenase, and the subsequent testing of the media in which the product and enzyme are incubated for soluble degradation products of the cross-linked product. The test is generally accomplished by pelletizing the undigested, cross-linked tissue by centrifugation and testing the resulting supernatant for degradation products.

Following photo-irradiation, the cross-linked product may be advantageously subjected to various treatments for the removal of the catalyst and other chemicals or impurities found therein before being used as a vascular graft. Multiple rinses in a fresh buffer solution, for example, may be used, followed by at least partial removal of water by treatment with, for instance, ethanol. The number of rinses and the volume of rinse solution required depends upon the mass of the tissue and the catalyst concentration utilized.

OTHER METHODS FOR THE FIXATION OF GRAFT TISSUE

In addition to the use of photooxidation processes for the fixation of the graft tissue, numerous other fixation methods have been described and are readily available in the art. For example, glutaraldehyde, and other related aldehydes, have seen widespread use in preparing cross-linked biological tissues. Glutaraldehyde is a five carbon aliphatic molecule with an aldehyde at each end of the chain, rendering it bifunctional. These aldehyde groups react under physiological conditions with primary amine groups on collagen molecules resulting in the cross-linking of collagen containing tissues. Methods for glutaraldehyde fixation of biological tissues have been extensively described and are well known in the art. In general, a tissue sample to be cross-linked is simply contacted with a glutaraldeyde solution for a duration effective to cause the desired degree of cross-linking within the biological tissue being treated.

Many variations and conditions have been applied to optimize glutaraldehyde fixation procedures. For example, lower concentrations have been found to be better in bulk tissue cross-linking compared to higher concentrations. It has been proposed that higher concentrations of glutaraldehyde may promote rapid surface cross-linking of the tissue, generating a barrier that impedes or prevents the further diffusion of glutaraldehdye into the tissue bulk. For most bioprosthesis applications, the tissue is treated with a relatively low concentration glutaraldehyde solution, e.g., typically between 0.1%–5%, for 24 hours or more to ensure optimum fixation. Of course, various other combinations of glutaraldehyde concentrations and treatment times will also be suitable depending on the objectives for a given application.

In addition to bifunctional aldehydes, many other chemical fixation procedures have been described (for review, see Khor, Biomaterials 18: 95–105, 1997). For example, some such methods have employed polyethers, polyepoxy compounds, diisocyanates, azides, etc. These and other approaches available to the skilled individual in the art for treating biological tissues will be suitable for cross-linking vascular graft tissue according to this invention.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A vascular graft, comprising:
a length of vascular tissue having a tubular structure;
a synthetic sleeve enclosing the vascular tissue, wherein the synthetic sleeve comprises woven, knitted or braided polymeric fibers or yarns, said synthetic sleeve having an extended length and a relaxed length, wherein the relaxed length is less than the extended length and the relaxed length is substantially similar to said length of vascular tissue; and wherein the length of vascular tissue and the synthetic sleeve are substantially longitudinally compliance-matched.

2. The vascular graft of claim 1, wherein the relaxed length of the synthetic sleeve is between about 50% and 95% of the extended length of the synthetic sleeve.

3. The vascular graft of claim 1, wherein the relaxed length of the synthetic sleeve is between about 70% and 90% of the extended length of the synthetic sleeve.

4. The vascular graft of claim 1, wherein the relaxed length of the synthetic sleeve is between about 75% and 95% of the extended length of the synthetic sleeve.

5. The vascular graft of claim 1, wherein the synthetic sleeve is crimped.

6. The vascular graft of claim 5, wherein the synthetic sleeve has a configuration that minimizes void spaces between vascular tissue and the synthetic sleeve following implantation and pressurization of the graft.

7. The vascular graft of claim 1, wherein n the synthetic sleeve has circumferential crimps along at least some portion of its longitudinal length.

8. The vascular graft of claim 1, wherein the synthetic sleeve has rounded crimps along at least some portion of its longitudinal length.

9. The vascular graft of claim 1, wherein the vascular tissue is derived from human, bovine, porcine, ovine, equine, canine or goat.

10. The vascular graft of claim 1, wherein the vascular tissue is derived from a carotid artery or thoracic artery.

11. The vascular graft of claim 1, wherein the vascular tissue is derived from a bovine carotid artery.

12. The vascular graft of claim 1, wherein the vascular tissue has been treated with one or more fixation techniques.

13. The vascular graft of claim 1, wherein the vascular tissue has been treated by photooxidation or chemical fixation.

14. The vascular graft of claim 1 wherein the synthetic sleeve is comprised of a polymeric material in the form of a tubular structure.

15. The vascular graft of claim 1, wherein the synthetic sleeve is comprised of at least one polyester, polypropylene, polyethylene, or polyurethane.

16. The vascular graft of claim 1, wherein the synthetic sleeve is comprised of polyethylene terepthalate or polytetrafluorethylene.

17. A vascular graft, comprising:

a length of vascular tissue having a tubular structure, said tissue having been treated by a photooxidation process;

a polyethylene terephthalate or polytetrafluorethylene synthetic sleeve enclosing the vascular tissue, said synthetic sleeve having rounded crimps along it longitudinal length, and said synthetic sleeve having an extended length and a relaxed length, wherein the relaxed length of the synthetic sleeve is between about 70% and 90% of the extended length of the synthetic sleeve and the relaxed length is substantially similar to said length of vascular tissue; and wherein the length of vascular tissue and the synthetic sleeve are substantially longitudinally compliance-matched.

18. The vascular graft of claim 17, wherein the synthetic sleeve has a configuration that minimizes void spaces between vascular tissue and the synthetic sleeve following implantation and pressurization of the graft.

19. The vascular graft of claim 17, wherein the relaxed length of the synthetic sleeve is between about 75% and 85% of the extended length of the synthetic sleeve.

20. The vascular graft of claim 17, wherein the vascular tissue is derived from human, bovine, porcine, ovine, equine, canine, or goat.

21. The vascular graft of claim 17, wherein the vascular tissue is derived from a carotid artery or thoracic artery.

22. The vascular graft of claim 17, wherein the vascular tissue is derived from a bovine carotid artery.

23. The vascular graft of claim 17, wherein the synthetic sleeve is comprised of woven, knitted and/or braided polymeric fibers or yarns.

24. A method for making a vascular graft, comprising:

providing a tubular synthetic sleeve having a first length;

longitudinally compressing the synthetic sleeve to a length less than about 50% of said first length and exposing the sleeve to a first heat treatment effective to introduce crimps in some portion of the sleeve;

stretching the longitudinally compressed synthetic sleeve to a second length between about 50 and 95% of said first length and exposing the sleeve to a second heat treatment, and inserting a length of vascular tissue within said sleeve, said length of vascular tissue being substantially similar to said second length, wherein the length of vascular tissue and the synthetic sleeve are substantially longitudinally compliance-matched.

25. The method of claim 24, wherein the synthetic sleeve has a configuration that minimizes void spaces between vascular tissue and the synthetic sleeve following implantation and pressurization of the graft.

26. The method of claim 24, wherein the first heat treatment is performed at a temperature in the range of about 110 to 140 degree C.

27. The method of claim 24, wherein the first heat treatment is performed at a pressure in the range of about 10 to 25 psi.

28. The method of claim 24, wherein the first heat treatment is performed for a duration in the range of about 0 to 0.5 hours.

29. The method of claim 24, wherein the second heat treatment is performed at a temperature in the range of about 110 to 140 degree C.

30. The method of claim 24, wherein the second heat treatment is performed at a pressure in the range of about 10 to 25 psi.

31. The method of claim 24, wherein the second heat treatment is performed for a duration in the range of about 0.1 to 0.5 hours.

32. The method of claim 24, wherein the second length of the synthetic sleeve is between about 75% and 85% of said first length.

33. The method of claim 24, wherein the synthetic sleeve after said first heat treatment has substantially angular crimps along its longitudinal length.

34. The method of claim 24, wherein the synthetic sleeve after said second heat treatment has substantially rounded crimps along its longitudinal length.

35. The method of claim 24, wherein the vascular tissue is derived from human, bovine, porcine, ovine, equine, canine, or goat.

36. The method of claim 24, wherein the vascular tissue is derived from a carotid artery or thoracic artery.

37. The method of claim 24, wherein the vascular tissue is derived from a bovine carotid artery.

38. The method of claim 24, wherein the vascular tissue has been treated with one or more fixation techniques.

39. The method of claim 24, wherein the vascular tissue has been treated by photofixation or chemical fixation.

40. The method of claim 24, wherein the synthetic sleeve is comprised of a polymeric material in the form of a tubular structure.

41. The method of claim 24, wherein the synthetic sleeve is comprised of woven, knitted and/or braided polymeric fibers or yarns in the form of a tubular structure.

42. The method of claim 24, wherein the synthetic sleeve is comprised of at least one polyester, polypropylene, polyethylene, or polyurethane.

43. The method of claim 24, wherein the synthetic sleeve is comprised of polyethylene terepthalate or polytetrafluorethylene.

44. A method for making a vascular graft, comprising:

providing a tubular polyethylene terephthalate or polytetrafluoroethylene sleeve having a first length;

longitudinally compressing the sleeve to a length less than about 50% of said first length and exposing the sleeve to a first heat treatment effective to introduce crimps in some portion of the sleeve;

stretching the longitudinally compressed synthetic sleeve to a second length between about 70% and 90% of said first length and exposing the sleeve to a second heat treatment, and inserting a length of photooxidized vascular tissue within said sleeve, said length of vascular tissue being substantially similar to said second length, wherein the length of vascular tissue and the synthetic sleeve are substantially longitudinally compliance-matched.

45. The method of claim 44, wherein the synthetic sleeve has a configuration that minimizes void spaces between vascular tissue and the synthetic sleeve following implantation and pressurization of the graft.

46. The method of claim 44, wherein the first heat treatment is performed at a temperature in the range of about 110 to 140 degree C.

47. The method of claim 44, wherein the first heat treatment is performed at a pressure in the range of about 10 to 25 psi.

48. The method of claim 44, wherein the first heat treatment is performed for a duration in the range of about 0 to 0.5 hours.

49. The method of claim 44, wherein the second heat treatment is performed at a temperature in the range of about 110 to 140 degree C.

50. The method of claim 44, wherein the second heat treatment is performed at a pressure in the range of about 10 to 25 psi.

51. The method of claim 44, wherein the second heat treatment is performed for a duration in the range of about 0.1 to 0.5 hours.

52. The method of claim 44, wherein the second length of the synthetic sleeve is between about 75% and 85% of said first length.

53. The method of claim 44, wherein the synthetic sleeve after said first heat treatment has substantially angular crimps along its longitudinal length.

54. The method of claim 44, wherein the synthetic sleeve after said second heat treatment has substantially rounded crimps along its longitudinal length.

55. The method of claim 44, wherein the vascular tissue is derived from human, bovine, porcine, ovine, equine, canine, or goat.

56. The method of claim 44, wherein the vascular tissue is derived from a carotid artery or thoracic artery.

57. The method of claim 44, wherein the vascular tissue is derived from a bovine carotid artery.

58. The method of claim 44, wherein the synthetic sleeve is comprised of woven, knitted and/or braided polymeric fibers or yams in the form of a tubular structure.

59. A vascular graft produced according to the method of claim 44.

* * * * *